United States Patent
Yeh et al.

(10) Patent No.: US 10,094,774 B2
(45) Date of Patent: *Oct. 9, 2018

(54) SCATTERING MEASUREMENT SYSTEM AND METHOD

(71) Applicant: Industrial Technology Research Institute, Hsinchu (TW)

(72) Inventors: Chia-Liang Yeh, Hsinchu (TW); Yi-Chang Chen, Hsinchu (TW); Yi-Sha Ku, Hsinchu (TW); Chun-Wei Lo, Hsinchu (TW)

(73) Assignee: INDUSTRIAL TECHNOLOGY RESEARCH INSTITUTE, Hsinchu County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/369,190

(22) Filed: Dec. 5, 2016

(65) Prior Publication Data

US 2017/0082536 A1 Mar. 23, 2017

Related U.S. Application Data

(63) Continuation-in-part of application No. 14/974,892, filed on Dec. 18, 2015.

(30) Foreign Application Priority Data

Aug. 12, 2015 (TW) .............................. 104126218 A
Aug. 12, 2016 (TW) .............................. 105125725 A

(51) Int. Cl.
*G01B 11/30* (2006.01)
*G01N 21/47* (2006.01)
(Continued)

(52) U.S. Cl.
CPC ......... *G01N 21/4788* (2013.01); *G01B 11/24* (2013.01); *G01N 21/4785* (2013.01);
(Continued)

(58) Field of Classification Search
CPC ... G01B 11/24; G01B 11/2433; G01B 11/245; G01B 11/306; G02B 21/0016
(Continued)

(56) References Cited

U.S. PATENT DOCUMENTS 5,703,692 A 12/1997 McNeil et al.
5,900,633 A 5/1999 Solomon et al.
(Continued)

FOREIGN PATENT DOCUMENTS

CN 1662788 A 8/2005
CN 102144182 A 8/2011
(Continued)

OTHER PUBLICATIONS

T. Harada et al., "The Coherent EUV Scatterometry Microscope for Actinic Mask Inspection and Metrology," Proc. of SPIE, vol. 8081, 2011, 9 pp.
(Continued)

*Primary Examiner* — Md M Rahman
(74) *Attorney, Agent, or Firm* — Muncy, Geissler, Olds & Lowe, P.C.

(57) ABSTRACT

A scattering measurement system is provided, including: a light source generator for generating a detection light beam with discontinuous multi-wavelengths, and generating a multi-order diffraction light beam with three-dimensional feature information when the detection light beam is incident on an object; a detector having a photosensitive array for receiving and converting the multi-order diffraction light beam into multi-order diffraction signals with the three-dimensional feature information; and a processing module
(Continued)

for receiving the multi-order diffraction signals and comparing the multi-order diffraction signals with multi-order diffraction feature patterns in a database so as to analyze the three-dimensional feature information of the object.

2 Claims, 8 Drawing Sheets

(51) Int. Cl.
  *G01B 11/24* (2006.01)
  *H01L 21/66* (2006.01)
(52) U.S. Cl.
  CPC ......... *G01N 21/4795* (2013.01); *H01L 22/00* (2013.01); *G01B 2210/56* (2013.01); *G01N 2201/068* (2013.01)
(58) Field of Classification Search
  USPC .......................................... 356/612
  See application file for complete search history.

(56) References Cited

U.S. PATENT DOCUMENTS

| | | | |
|---|---|---|---|
| 6,320,658 | B1 | 11/2001 | Mizutani |
| 6,633,831 | B2 | 10/2003 | Nikoonahad et al. |
| 7,593,119 | B2 | 9/2009 | Niu et al. |
| 8,543,557 | B2 | 9/2013 | Aikens et al. |
| 2002/0033945 | A1* | 3/2002 | Xu ..................... G01B 11/0641 356/369 |
| 2012/0081684 | A1 | 4/2012 | Den Oef et al. |
| 2012/0123581 | A1* | 5/2012 | Smilde ................ G03F 7/70483 700/105 |
| 2013/0016362 | A1* | 1/2013 | Gong ................. G01B 11/2527 356/610 |
| 2014/0146322 | A1 | 5/2014 | Hill et al. |
| 2015/0192463 | A1* | 7/2015 | Jhon ..................... G01J 3/0297 250/252.1 |

FOREIGN PATENT DOCUMENTS

| | | |
|---|---|---|
| CN | 103649677 A | 3/2014 |
| EP | 1092145 A1 | 4/2001 |
| TW | 201043917 A | 12/2010 |
| TW | I358529 B | 2/2012 |
| TW | 201508240 A | 3/2015 |
| WO | WO00/00817 | 1/2000 |
| WO | WO 2015/175900 A1 | 11/2015 |

OTHER PUBLICATIONS

H. Vu Le et al., "Generation of highly coherent extreme ultraviolet source and its application in diffraction imaging," Results in Physics 4, 2014, pp. 113-116.
P.M. Paul et al., "Observation of a Train of Attosecond Pulses from High Harmonic Generation," Science, vol. 292, Jun. 1, 2001, pp. 1689-1692.
S. Teichmann, "High Harmonic Generation for Coherent Diffractive Imaging," thesis for the degree of Doctor of Philosophy, Centre for Atom Optics and Ultrafast Spectroscopy and ARC Centre of Excellence for Coherent X-Ray Science, Nov. 25, 2009, 246 pp.
T. Harada et al., "Development of standalone coherent EUV scatterometry microscope with high-harmonic-generation EUV source," Proc. of SPIE, vol. 8441, 2012, 10 pp.

* cited by examiner

SCATTERING MEASUREMENT SYSTEM AND METHOD

CROSS-REFERENCE TO RELATED APPLICATION

This application is a continuation-in-part (CIP) of U.S. patent application Ser. No. 14/974,892, filed on Dec. 18, 2015, which claims the benefit of Taiwan Application No. 104126218, filed on Aug. 12, 2015 and Taiwan Application No. 105125725, filed on Aug. 12, 2016. The entirety of the above-mentioned patent applications are hereby incorporated by reference herein and made a part of this specification.

TECHNICAL FIELD

The technical field relates to a scattering measurement system and method for measuring a three-dimensional structure, and, more particularly, to a nano-scaled scattering measurement system and method for measuring a three-dimensional structure.

BACKGROUND

It is described in the 2013 edition of ITRS (International Technology Roadmap for Semiconductors) Metrology Summary that FinFETs are now the dominant key element architecture of advanced microprocessors and both FinFETs and other three-dimensional structure measurement technologies are facing the challenges of reduced size and increased aspect ratio.

Current nanoscale measurement instruments such as CD-SEMs and CD-AFMs only provide a two-dimensional (X-axis and Y-axis) measurement of a surface structure, which are limited in providing a third dimensional (Z-axis) measurement. Therefore, dimensions such as the line width, the height and the sidewall angle of a three-dimensional structure having a high aspect ratio cannot be obtained. To overcome the drawback, a measurement method is proposed. A conventional measurement method involves emitting a light beam from a light source generator onto an object through a light focusing element. Then, the light beam passes through a lens and is collected by a camera. With the rotation of a prism, the incident angle of the light beam incident on the object is changed. The light beam is scattered and dispersed by the object to generate multi-order diffraction signals, and zero-order (0th-order) signals of the multi-order diffraction signals are measured. Based on the correlation between the 0th-order signals and the incident angles, a feature spectrum is generated to facilitate analysis of the three-dimensional structure of the object. However, in the above-described measurement method, an error of the rotating mechanism appears in the measurement result. In addition, the measurement process is time-consuming. According to another conventional measurement method, a light beam from a broadband light source is incident on an object with a fixed angle. The light beam is then scattered by the object to generate multi-order diffraction signals. 0th-order signals of the multi-order diffraction signals are captured and then dispersed by a spectrometer. As such, the distribution of diffraction intensities at different wavelengths is measured to facilitate analysis of the three-dimensional structure of the object. However, after the light passes through a dispersive element and a slit of the spectrometer, the light intensity decays significantly that adversely affects the measurement accuracy. Therefore, in the above-described measurement methods, the measurement accuracy is reduced either by an error of the rotating mechanism or by a significant decay of the light intensity after the light passes through a dispersive element.

Therefore, if the three-dimensional structure of an object (including the Z-axis dimension) can be quickly and accurately measured based on a theoretical model of a laser light scattering device and hardware experiences with the laser light scattering device as well as EUV (extreme ultraviolet) scattering device technologies, measurement of future nanoscale objects will be facilitated. It has become urgent to solve this issue.

SUMMARY

An embodiment of the disclosure relates to a scattering measurement system, which comprises: a light source generator configured to generate a detection light beam with discontinuous multi-wavelengths, and generate multi-order diffraction light beams with three-dimensional feature information as the detection light beam is incident on an object; a detector having a photosensitive array and configured to receive and convert the multi-order diffraction light beams into multi-order diffraction signals with the three-dimensional feature information; and a processing module configured to receive the multi-order diffraction signals and compare the multi-order diffraction signals with multi-order diffraction feature patterns in a database so as to analyze the three-dimensional feature information of the object.

According to one embodiment, the present disclosure further provides a scattering measurement method, which comprises the steps of: providing a detection light beam with discontinuous multi-wavelengths to an object, to generate a multi-order diffraction light beam as the detection light beam passes the object; receiving and converting, by a photosensitive array, the multi-order diffraction light beams into multi-order diffraction signals with the three-dimensional feature information; and comparing the multi-order diffraction signals with multi-order diffraction feature patterns in a database to analyze the three-dimension feature information of the object.

The foregoing will become better understood from a careful reading of a detailed description provided herein below with appropriate reference to the accompanying drawings.

DETAILED DESCRIPTION

The following illustrative embodiments are provided to illustrate the present disclosure. These and other advantages and effects can be apparent to those in the art after reading this specification. It should be noted that all the drawings are not intended to limit the present disclosure. Various modifications and variations can be made without departing from the spirit of the present disclosure.

Figure 1:
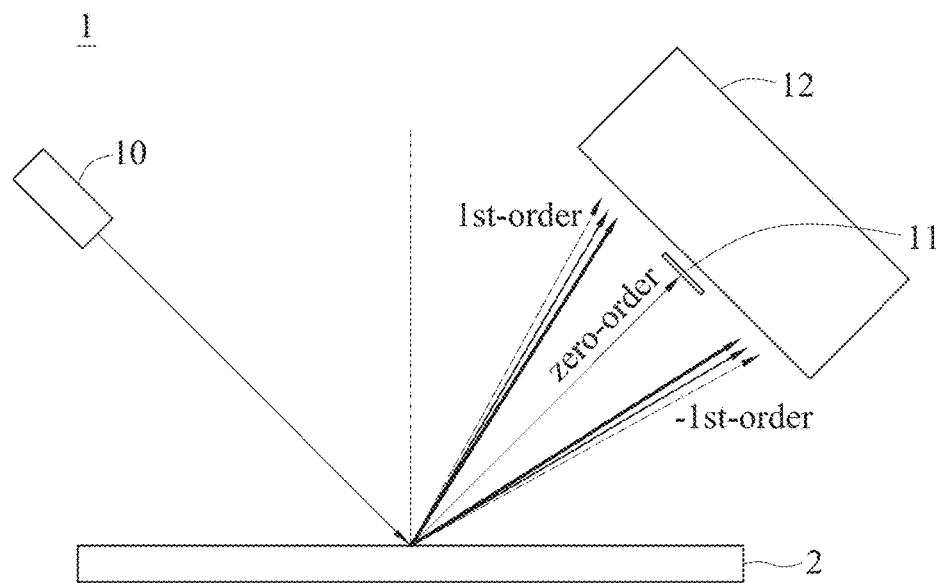
FIG. 1 is a schematic diagram of a scattering measurement system according to an exemplary embodiment of the present disclosure.

FIG. 1 is a schematic diagram of a scattering measurement system according to an exemplary embodiment of the disclosure. FIG. 1 shows the operation principle of the scattering measurement system. Referring to the embodiment in FIG. 1, the scattering measurement system 1 includes a light source generator 10, a spatial filter 11 and a detector 12.

The light source generator 10 generates a detection light beam with multi-wavelengths. The detection light beam is incident on an object 2 so as to generate a plurality of multi-order diffraction light beams with three-dimensional feature information. In practice, the wavelength band of the detection light beam generated by the light source generator 10 can be determined according to the dimension of the object 2. For example, if the object is a FinFET having a nanoscale dimension, the light source generator 10 can be a light projecting device projecting a light source having multi-wavelengths within a narrow band, including a EUV (extreme ultraviolet) band.

In an embodiment, the multi-wavelengths of the detection light beam are discontinuous. In one embodiment, the present disclosure uses an HHG (High-order Harmonic Generation) EUV light beam with discontinuous multi-wavelengths. The HHG EUV light beam is incident on the object 2 through a focusing mirror.

The spatial filter 11 is used to filter out 0th-order diffraction light beams from the multi-order diffraction light beams, which are scattered by the object 2. In one embodiment, the spatial filter 11 has a low transmission filter for filtering out the 0th-order diffraction light beams. By filtering out the 0th-order diffraction light beams from the multi-order diffraction light beams, the present embodiment of the disclosure uses the multi-order diffraction light beams with the 0th-order diffraction light beams filtered out for subsequent analysis, instead of merely using the 0th-order diffraction light beams as in the prior art, but the disclosure is not limited thereto. Further, the position of the 0th-order diffraction light beams or the non-zero order diffraction light beams can be calculated according to the scattering law.

Generally, since the signal intensity of the 0th-order diffraction light beams is greater than the signal intensity of the other non-zero order diffraction light beams, the conventional methods use the 0th-order diffraction light beam signals for analysis and the other non-zero order diffraction light beam signals are regarded as noises. The conventional methods can be used to measure large-scale objects by measuring 0th-order signals at a plurality of angles using a single wavelength beam or measuring 0th-order signals using a multi-wavelengths beam, and generating 1st-order signals at a fixed position through an optical element for subsequent analysis. However, since the 0th-order signals may not have sufficient sensitivity for small-scale objects such as FinFETs, the above-described methods may not be easily applied in measuring small-scale objects.

The present embodiment of FIG. 1 is used to measure small-scale objects. The present embodiment filters out the 0th-order diffraction light beams and uses the multi-wavelength multi-order diffraction light beams without the 0th-order diffraction light beams, for example, 1st-order light beams (i.e., +1st-order and/or −1st-order light beams as shown in FIG. 1) for analysis. Generally, the intensity of the 0th-order diffraction light beams may be greater than the intensity of the non-zero order light beams, if the detector receives only the 0th-order diffraction light beams, the detector may become over-saturated that adversely affects the analysis accuracy. After the detection light beam is scattered by the object, the non-zero order (e.g., the 1st-order) diffraction light beams also include the three-dimensional structure information of the object. In an embodiment, for a small-scale object, e.g., a nanoscale or smaller object, the 1st-order diffraction light beam signals with multi-wavelengths are sufficient to be detected by the detector, and therefore the 0th-order diffraction light beams may not be needed. In addition, the conventional light dispersion process can be omitted so as to simplify the scattering measurement process and architecture.

The detector 12 has a photosensitive array for receiving the plurality of multi-order diffraction light beams filtered out by the spatial filter 11 and converting the filtered multi-order diffraction light beams into multi-order diffraction signals with the three-dimensional feature information. The photosensitive array of the detector 12 is, for example, a CCD or CMOS array. The detector 12 receives the multi-order diffraction light beams filtered out by the spatial filter 11. At this point, the multi-order diffraction light beams received by the detector 12 do not include any 0th-order diffraction light beams. The multi-order diffraction light beams (i.e., multi-wavelength non-zero order diffraction light beams) received by the detector 12 may not need to be dispersed as in the prior art. The detector 12 can convert the multi-order diffraction light beams with the three-dimensional feature information into multi-order diffraction signals with the three-dimensional feature information.

Therefore, in the embodiment of FIG. 1, the scattering measurement system can be used to measure a small-scale object, e.g., a nanoscale object. By filtering out multi-wavelength 0th-order diffraction light beams and capturing multi-wavelength multi-order diffraction light beams, the present disclosure obtains the three-dimensional feature information of the object. As compared with the known prior art, the present embodiment may simplify the measurement process and be capable of quickly obtaining the three-dimensional structure of the object with high resolution.

Figure 2:
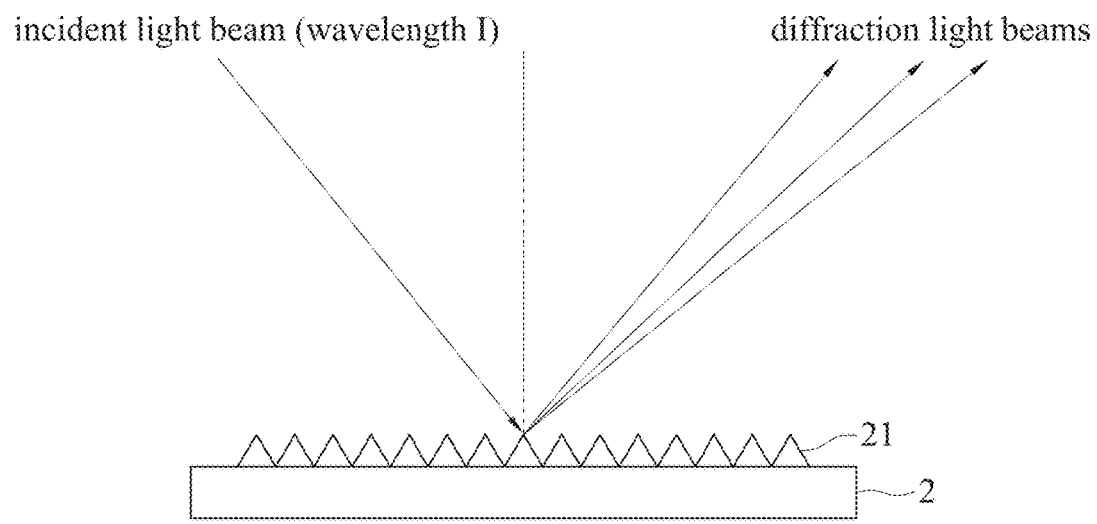
FIG. 2 is a schematic diagram of the scattering theory according to an exemplary embodiment of the disclosure.

FIG. 2 is a schematic diagram showing the scattering theory according to an embodiment of the present disclosure. According to the scattering theory, when a light beam is incident on the object 2, the intensity and position of the scattered light are dependent on the incident angle or wavelength of the light beam, thereby generating a feature pattern. For example, when the object 2 having a periodically arranged grating structure 21 is irradiated by a light source, its scattering pattern is closely correlated with the grating structure. By analyzing the scattering pattern, the shape and structure parameters of the diffraction grating can be obtained.

Based on Maxwell's equations, the scattering pattern can be accurately converted into the average features of the isometric grating, such as the CD (critical dimension), the sidewall angle, the film thickness, the pitch of the grating and so on. Currently, there are two kinds of architectures used for scattering devices in semiconductor process measurement: a multi-angle scattering device architecture using a single-wavelength laser light incident at a plurality of angles, and an ellipsometer or reflectometer architecture using a multi-wavelength light source incident at a single angle.

Further, embodiments of the present disclosure enable a light beam with discontinuous multi-wavelengths or discrete wavelengths to be incident on an object to thereby collect multi-order scattering signals. When light is scattered by a periodic structure to generate light beams with a plurality of diffraction orders, the diffraction light beams are distributed at different angles in space according to the grating equation, which is shown as the following equation 1:

$$\sin q_i + \sin q_n = n\lambda/d \qquad \text{equation 1,}$$

Wherein $q_i$ represents an incident angle, $q_n$ represents a distribution angle of an $n^{th}$-order diffraction light beam in the space, $\lambda$ represents the wavelength of an incident light beam, and d represents the periodic size of the grating structure. Based on the diffraction theory, changes of the scattering pattern caused by variations of structure parameters can be calculated. A software model is established based on the theory for analyzing and comparing the pattern so as to provide data of the structure.

In principle, since the interaction between the incident light beam and the periodic grating structure is quite complicated, the energy of the incident light beam diffracted to different diffraction orders in space is quite sensitive to the size of the periodic grating structure, such that the feature of the grating structure can be measured.

Therefore, the present disclosure enables a light beam with discontinuous multi-wavelengths to be incident on the object 2 to generate multi-order diffraction signals. In one embodiment, 0th-order signals are filtered out from the multi-order diffraction signals by the spatial filter, but not limited thereto, and the multi-wavelength non-zero order diffraction signals are received by the detector.

To obtain the three-dimensional structure of the object 2, the scattering measurement system of the present embodiment further has a comparison unit (not shown) disposed in an electronic device (such as a computer, a server, and the like) connected/coupled to the detector 12 of FIG. 1. The comparison unit is used to compare the multi-order diffraction signals with multi-order diffraction feature patterns in a database so as to obtain a three-dimensional structure of the object 2 corresponding to the multi-order diffraction signals. The multi-order diffraction signals refer to the multi-order diffraction signals with/without 0th-order signals filtered out by the spatial filter. The comparison unit may be implemented in a form of software, firmware or hardware by employing a general programming language (e.g., C or C++), a hardware description language (e.g., Verilog HDL or VHDL) or other suitable programming languages. The software (or firmware) capable of executing the functions may be deployed in an electronic device accessible media, such as magnetic tapes, semiconductor memories, magnetic disks or compact disks (e.g., CD-ROM or DVD-ROM) or may be delivered through the Internet, wired communication, wireless communication or other communication media. The software (or firmware) may be stored in the electronic device accessible media for a processor of the electronic device to access/execute the programming codes of the software (or firmware). Moreover, the apparatus and method provided in the disclosure may be implemented by combination of hardware and software.

In one embodiment, the multi-order diffraction feature patterns are multi-wavelength multi-order diffraction feature patterns that are established based on a rigorous coupled-wave theory.

In an embodiment, to remove a measurement error caused by instability of the light source, any two multi-order signals having a same wavelength can be divided by one another. Because of the correlation between the light wavelengths and the dimension of the object, the light wavelengths at nanoscale are quite short, which results in poor stability of the light. Therefore, based on the proportional relationship between multi-orders at each wavelength, the present disclosure reduces the measurement error caused by instability of the light source.

For example, the light intensities of the 1st-order signals $\lambda 1$, $\lambda 2$, and $\lambda 3$ are 0.5, 0.6, and 0.7, respectively, and the light intensities of the $2^{nd}$-order signals $\lambda 1$, $\lambda 2$, and $\lambda 3$ are 0.6, 0.7, and 0.8, respectively. If the light source changes, the light intensities of the 1st-order signals $\lambda 1$, $\lambda 2$, and $\lambda 3$ are 0.6, 0.7, and 0.8, respectively, and the light intensities of the $2^{nd}$-order signals $\lambda 1$, $\lambda 2$, and $\lambda 3$ are 0.7, 0.8, and 0.9, respectively. As such, any two of the multi-order signals are divided by one another to determine whether the light source is stable. That is to say, if a measurement error occurs, it can be determined whether it is caused by instability of the light source.

According to the prior art, only the 0th-order light beam signals are captured, and only one set of light intensity data can be obtained each time. Even if another set of light intensity data is obtained later, it cannot be determined whether the light source is stable due to the lack of a comparison basis.

Therefore, the use of multi-order signals facilitates to remove the measurement error caused by instability of the light source.

Further, a database is established based on a rigorous coupled-wave theory to compare the signals with feature patterns so as to analyze the three-dimensional structure of the object or obtain the structural information of the object in an inverse way according to the diffraction theory. Through computerized operation, a comparison database can be established by collecting a lot of diffraction patterns formed through variations of various kinds of parameters. After being established, the comparison database can be used for analysis and comparison. That is to say, after obtaining scattering data, the measurement system compares the scattering data with the data of the database so as to find the closest model data.

Figure 3A:
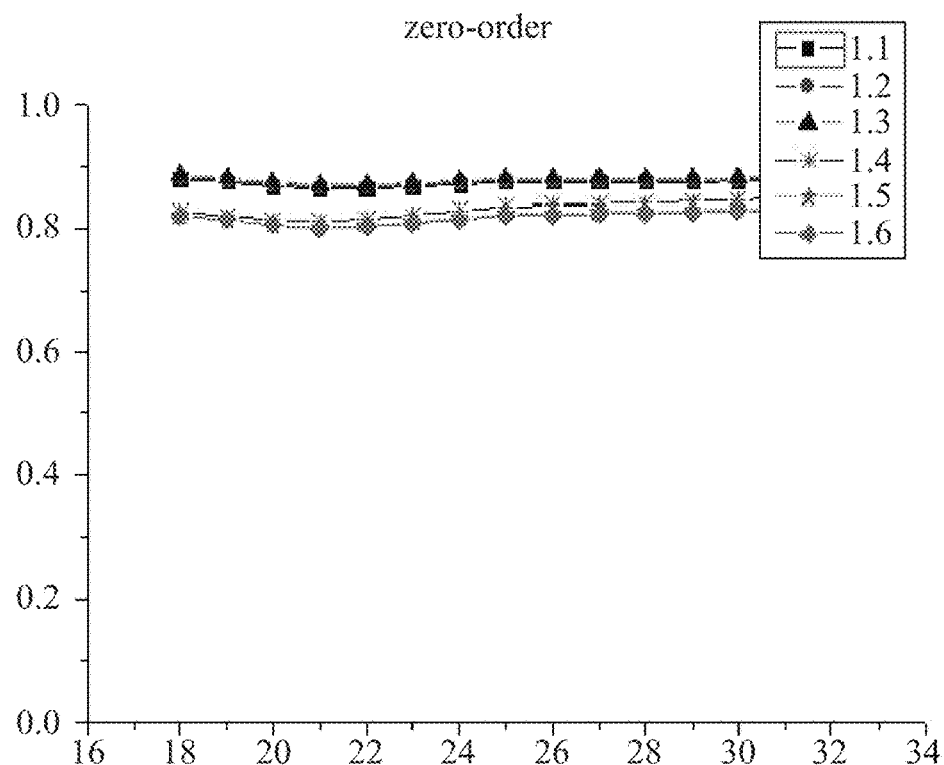
FIGS. 3A and 3B are a pair of graphs showing distribution of 0th-order signals and 1st-order signals of different wavelengths according to an exemplary embodiment of the disclosure.
Figure 3B:
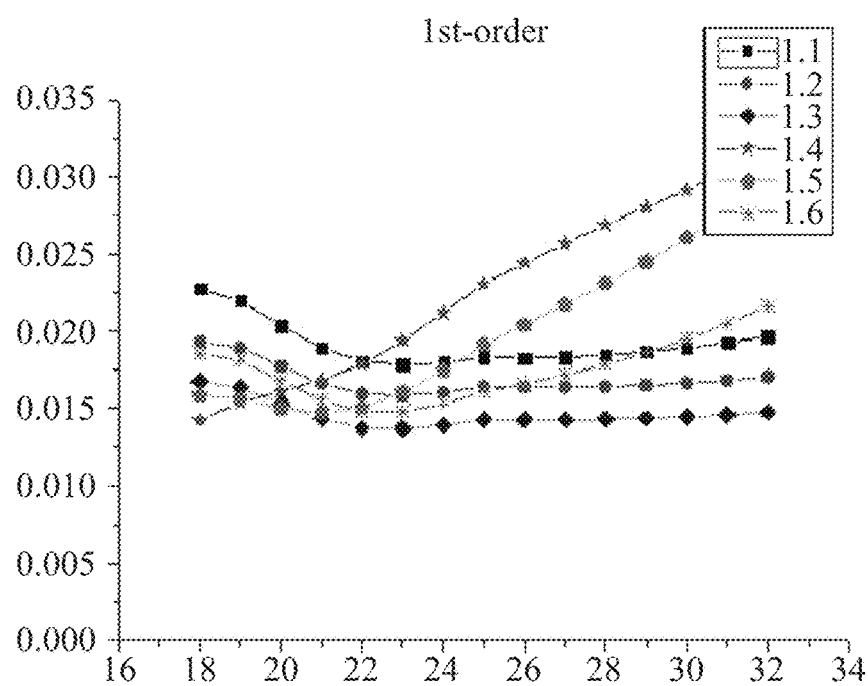

FIGS. 3A and 3B are two graphs showing distribution of 0th-order signals and 1st-order signals of different wavelengths according to an embodiment of the present disclosure. Referring to FIG. 3A, an object having a grating periodic pitch of about 50 nm is measured, and the relationship between the light wavelength and intensity of multi-wavelength 0th-order signals is shown. Referring to FIG. 3A, the light intensities of the 0th-order signals of different wavelengths (from 1.1 to 1.6) cannot be clearly differentiated, which increases the subsequent analysis difficulty.

FIG. 3B shows the relationship between the light wavelength and intensity of non-zero order signals with multi-wavelengths. It is noted that the 1st-order signals are exemplified. Referring to FIG. 3B, the light intensities of the 1st-order signals of different wavelengths (from 1.1 to 1.6) can be clearly differentiated, which facilitates the subsequent analysis.

Therefore, using multi-wavelength non-zero order signals is advantageous in measuring small-sized structures, but the disclosure is not limited thereto.

Figure 4A:
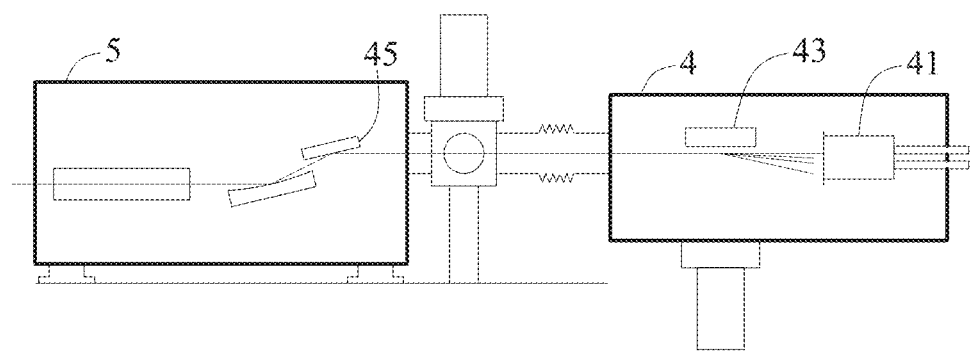
FIGS. 4A and 4B are two schematic diagrams showing operation of the scattering measurement system according to an exemplary embodiment of the disclosure.
Figure 4B:
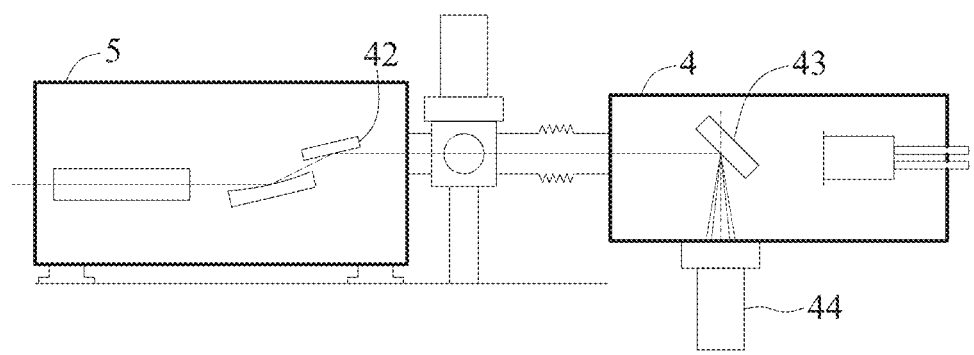

FIGS. 4A and 4B are two schematic diagrams showing operation of the scattering measurement system according to an embodiment of the present disclosure. Referring to FIGS. 4A and 4B, a light source generator 5 provides a detection light beam. The light source generator 5 can be a spectrometer, e.g., a Hettrick Scientific soft X-ray spectrometer. A measurement device 4 includes a first set of photosensitive devices 41 and a second set of photosensitive devices 44.

FIG. 4A shows operation for determining whether the light source is normal or stable. Whether the light source is normal can be determined through a comparison between current and previous data, and whether the light source is stable can be observed in a time period. During the process, the detection light beam is scattered by the grating 45 of the light source generator 5. The object 43 does not affect the transmission of the light beam. In one embodiment, the light beam from the light source generator 5 directly enters the measurement device 4, and is received by the first set of photosensitive devices 41, such that the light source instead of the object 43 is measured during this process.

As shown in FIG. 4B, the object 43 is rotated by an angle of about 45 degree. The grating 45 of the light source generator 5 is replaced by a reflective element 42. The light beam is reflected by the reflective element 42, entering the measurement device 4 and diffracted by the object 43 so as to generate diffraction light beams. The diffraction light beams are received by the second set of photosensitive devices 44.

Therefore, after the light source is measured and determined as stable, the orientation of the object 43 is changed by an angle so as to be measured. In one example, the second set of photosensitive devices 44 receives the diffraction light beams for analysis and comparison. The comparison refers to a comparison between the diffraction light beam signals and feature patterns of the above-described database.

Figure 5A:
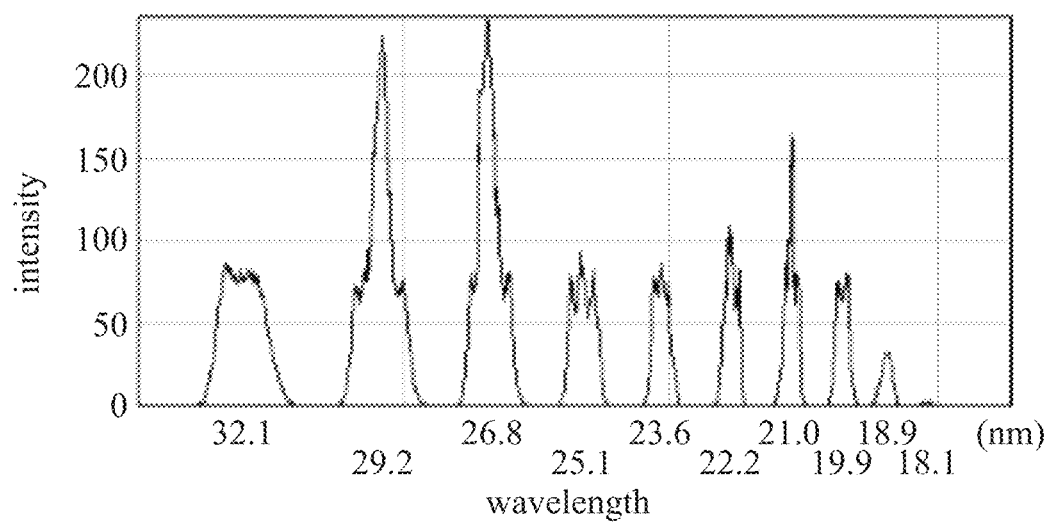
FIGS. 5A to 5E are schematic diagrams showing reconstruction of the three-dimensional structure of an object according to an exemplary embodiment of the disclosure.

FIGS. 5A to 5E are schematic diagrams showing detailed operation of the scattering measurement system according to an embodiment of the present disclosure. FIG. 5A represents the measurement result of the second set of photosensitive devices 44 of FIG. 4B, i.e., the multi-wavelength non-zero order (e.g., the 1st-order) diffraction light beams diffracted by the object 43, which are defined as I.

Figure 5B:
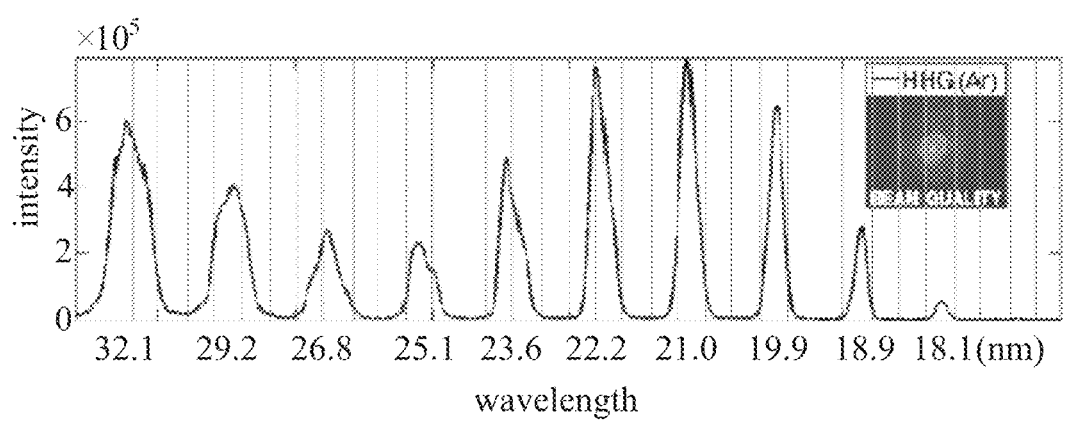

FIG. 5B shows the measurement result of the first set of photosensitive devices 41 of FIG. 4A, i.e., the multi-wavelength light source that does not pass through the object 43 but is only diffracted by the grating 45, which is defined as $I_0$.

Figure 5C:
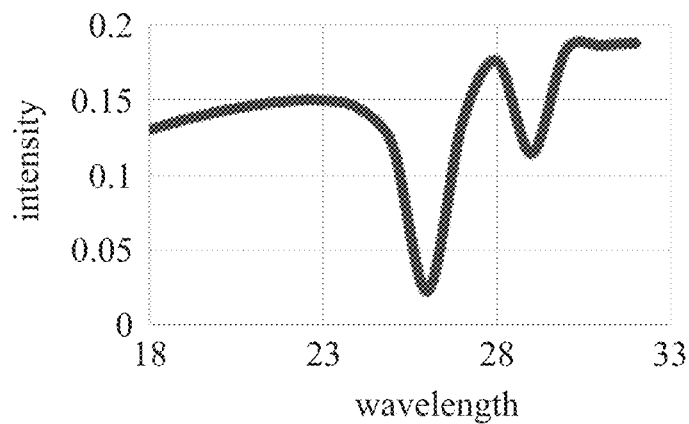

FIG. 5C shows feature pattern signals of the object 43 generated by dividing the multi-order diffraction light beams I with the multi-wavelength light source $I_0$. It should be noted that both FIG. 5A and FIG. 5B have nine discontinuous wavelengths. After the division operation, there should be 9 points in FIG. 5C. However, for the purpose of easy understanding, the points are connected into a continuous curve.

Figure 5D:
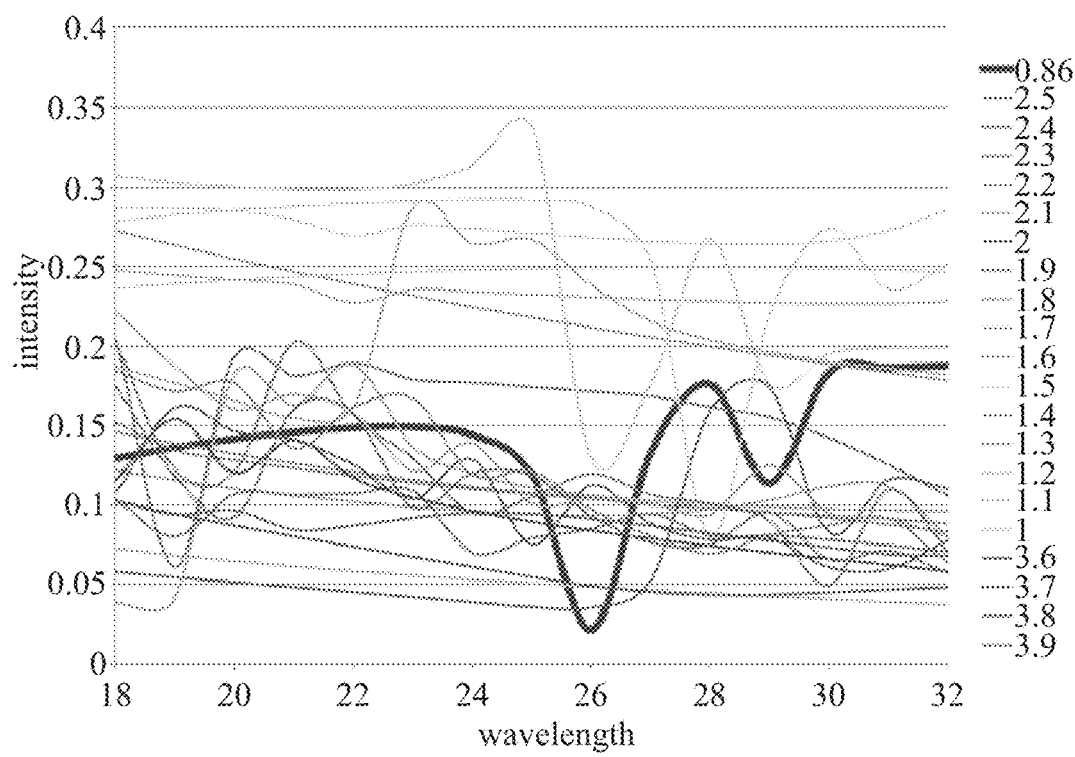
Figure 5E:
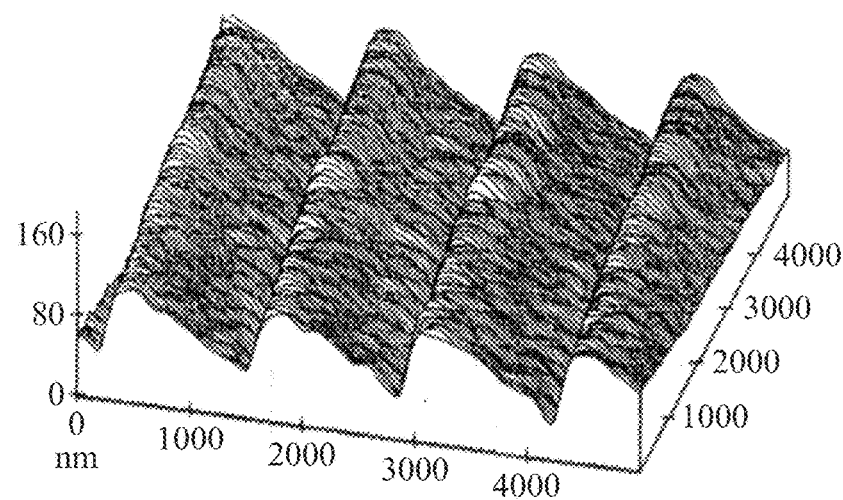

FIG. 5D shows a comparison database with a plurality of multi-order diffraction feature patterns pre-stored therein, i.e., three-dimensional feature signals obtained after a multi-wavelength light beam is diffracted by an object. The feature signals of the object 43 of FIG. 5A are compared with the database of FIG. 5B to find the matching one. Accordingly, the three-dimensional structure of the object is obtained, as shown in FIG. 5E.

Figure 6:
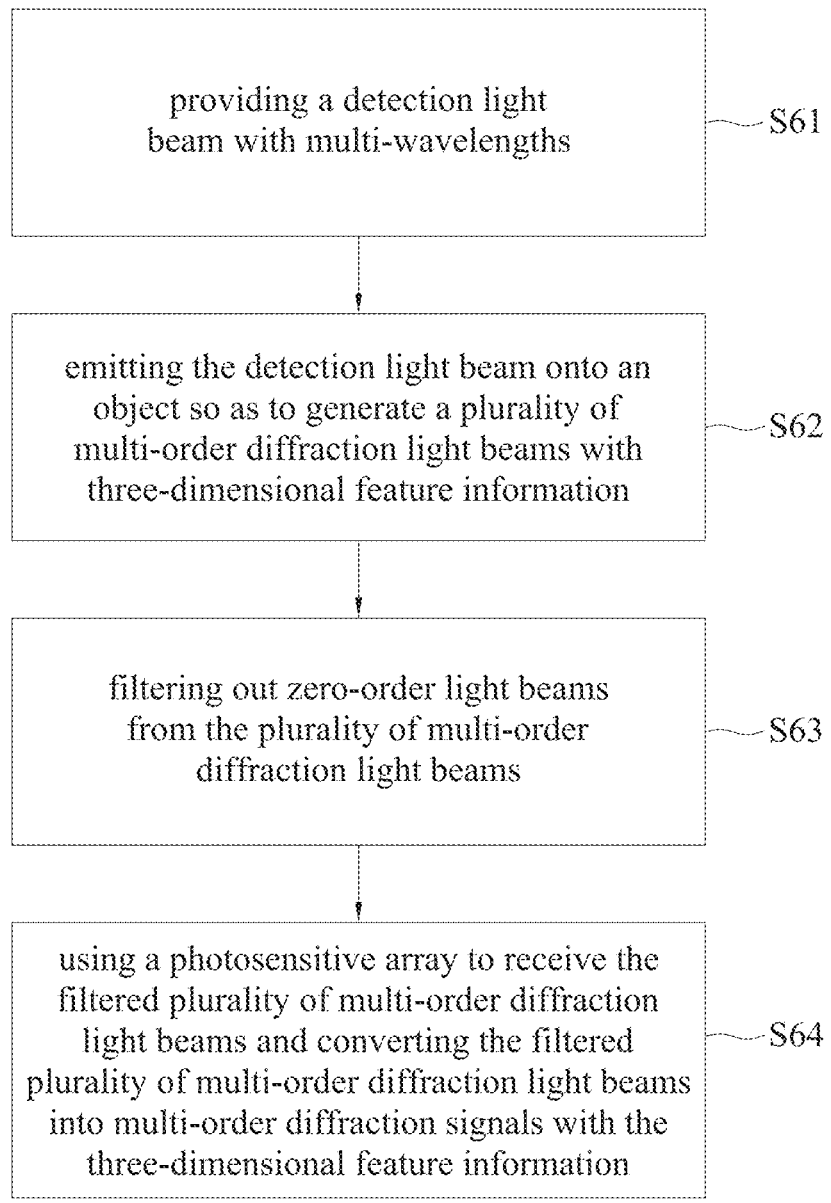
FIG. 6 is a schematic flow diagram showing a scattering measurement method according to an exemplary embodiment of the disclosure.

FIG. 6 is a schematic flow diagram showing a scattering measurement method according to an embodiment of the present disclosure. The scattering measurement method involves emitting a multi-wavelength detection light beam onto an object to be measure so as to generate a plurality of multi-order diffraction light beams with three-dimensional feature information. Then, a photosensitive array receives the plurality of multi-order diffraction light beams with 0th-order diffraction light beams filtered out, and converts the received plurality of multi-order diffraction light beams into multi-order diffraction signals with the three-dimensional feature information. The process is detailed as follows.

At step S61, a multi-wavelength detection light beam is provided. In practice, the multi-wavelength detection light beam is a detection light beam with discontinuous wavelengths, e.g., an HHG EUV light beam with discontinuous multi-wavelengths.

At step S62, the multi-wavelength light beam is incident on an object, thereby generating a plurality of multi-order diffraction light beams with three-dimensional feature information. In one example, after the detection light beam is incident on the object, the incident light is scattered by the object so as to generate a plurality of light beams with multiple diffraction orders. The scattered light beams include three-dimensional feature information of the object which refers to as multi-order diffraction light beams with three-dimensional feature information.

At step S63, 0th-order diffraction light beams are filtered out from the plurality of multi-order diffraction light beams. At this step, a low transmission filter is used to filter out the 0th-order diffraction light beams. Instead of using the 0th-order diffraction light beams, the present disclosure uses the non-zero order light beams, e.g., the 1st-order diffraction light beams, for subsequent analysis. As described above, using non-zero order signals is advantageous in measuring small-sized structures.

At step S64, a photosensitive array is used to receive the plurality of multi-order diffraction light beams with the 0th-order diffraction light beams filtered out and convert the filtered plurality of multi-order diffraction light beams into multi-order diffraction signals with the three-dimensional feature information. The photosensitive array can be, for example, a CCD array. The diffraction light beams with the 0th-order diffraction light beams filtered out do not need to be dispersed as in the prior art. The photosensitive array receives the diffraction light beams with the 0th-order diffraction light beams filtered out and converts the filtered diffraction light beams into multi-order diffraction signals with the three-dimensional feature information for subsequent analysis or comparison, thereby reconstructing the three-dimensional structure of the object.

The scattering measurement method of the present disclosure further includes comparing the multi-order diffraction signals with a plurality of pre-set multi-order diffraction feature patterns so as to obtain a three-dimensional structure of the object corresponding to the multi-order diffraction signals. In one example, after the multi-order diffraction signals are obtained, they are compared with a pre-established comparison database. The comparison database has multi-order diffraction feature patterns of different multi-wavelengths that are established based on a rigorous coupled-wave theory. Through such a comparison, the three-dimensional structure of the object can be obtained.

Figure 7:
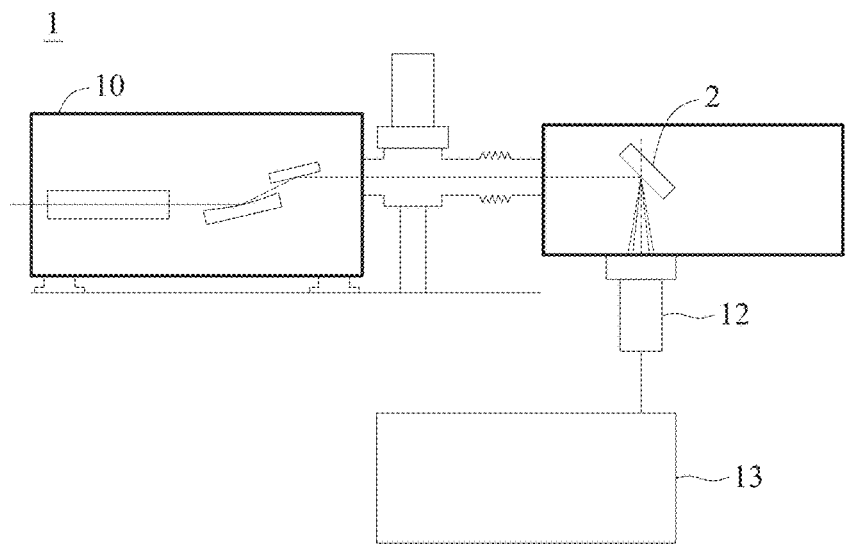
FIG. 7 is a schematic diagram of a scattering measurement system according to an exemplary embodiment of the disclosure.

FIG. 7 is a schematic flow diagram showing a scattering measurement system according to an embodiment of the present disclosure, the scattering measurement system in the embodiment is similar to the one illustrated in FIG. 1. It is noted, in the embodiment, the 0th-order diffraction light beams are not filtered out by a spatial filter, and in the embodiment the 0th-order diffraction light beams of the object are not filtered out. Referring to the embodiment in FIG. 7, the scattering measurement system 1 includes a light source generator 10, a detector 12 and a processing device 13. In the embodiment, the detector 12 receives the multi-order diffraction light beams including the 0th-order diffraction light beams.

In the embodiment of FIG. 7, the light source generator 10 generates a detection light beam with discontinuous multi-wavelengths (i.e., HHG EUV light beam with discrete multi-wavelengths). The detection light beam is used to be projected onto an object 2, as shown in FIG. 2. The detector 12 has a photosensitive array for receiving the multi-order diffraction light beams with the multi-wavelengths and converting the multi-order diffraction light beams into multi-order diffraction signals with the three-dimensional feature information.

In an embodiment, the photosensitive array of the detector 12 is a Charge Coupled Device (CCD) or a Complementary Metal Oxide Semiconductor (CMOS) array sensor. In another embodiment, the photosensitive array of the detector 12 is a one-dimensional linear array sensor (e.g., a linear CCD or linear CMOS sensor) or a two-dimensional array sensor (e.g., a flat CCD or flat CMOS sensor).

It is known from FIG. 2 and the aforementioned equation 1 that the detection light beam with discontinuous multi-wavelengths in the embodiment of FIG. 7 is projected onto an object (e.g., the object 2 having a periodically arranged grating structure 21), and the brightness and position of the diffraction light diffracted by the object 2 have different feature patterns based on the incident angles and wavelengths of the incident light beams. Therefore, information including the CD (critical dimension), the sidewall angle, the film thickness, the pitch of the grating, the depth or height, and the line-width of the measured object 2 can be obtained by analyzing the multi-order diffraction signals provided from the detector 12.

In the embodiment of FIG. 7, the processing device 13 can compare the multi-order diffraction signals output by the detector 12 with pre-set multi-order diffraction feature patterns stored in a database so as to obtain a three-dimensional structure of the object 2 corresponding to the multi-order diffraction signals. In the embodiment, the processing device 13 may be a computer and receive information output from the detector 12 wirely or wirelessly. In an embodiment, the database, stored with pre-set multi-order diffraction feature patterns, may be a storage device. In another embodiment, the storage device of the database is, but not limited to, a memory device embedded in the processing device 13. In an embodiment, the memory device may be a remote storage device (i.e., a cloud-based hard disk). The processing device 13 may access the multi-order diffraction feature patterns in the database in a wired or wireless manner.

Figure 8:
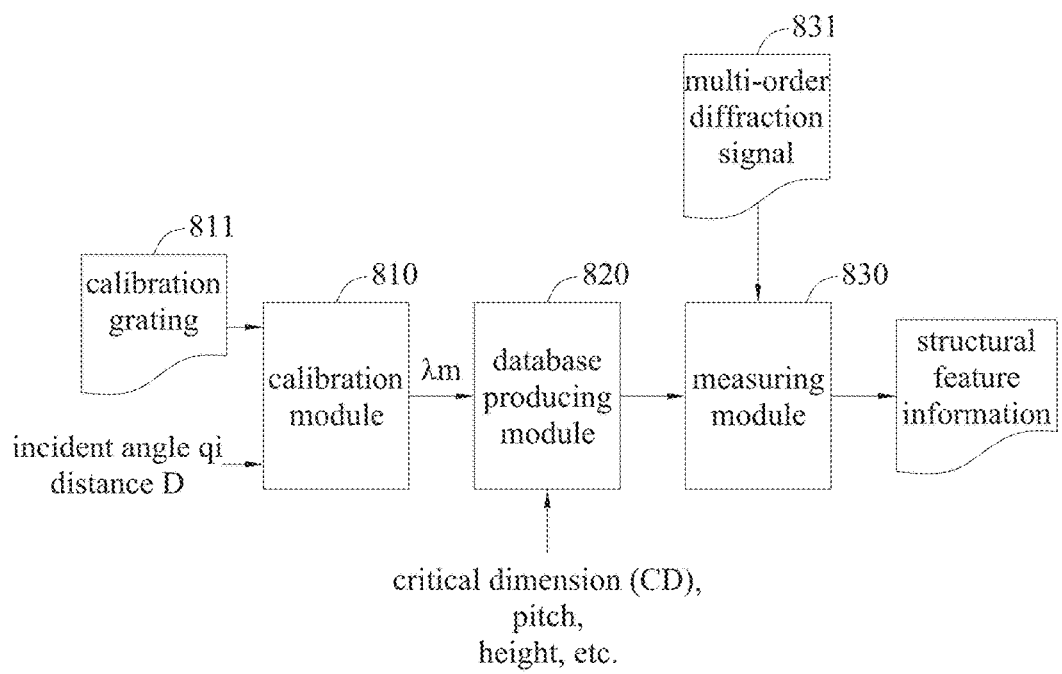
FIG. 8 is a schematic diagram illustrating each processing modules of the scattering measurement system in FIG. 7 according to an exemplary embodiment of the disclosure.

FIG. 8 is a schematic block-diagram illustrating each processing module of the scattering measurement system in FIG. 7 according to an embodiment of the disclosure. In the embodiment, a calibration module 810 is used to calibrate wavelengths of the light source generator 10 in the diffraction measurement system. A database producing module 820 is used to produce multi-order diffraction feature patterns based on a rigorous coupled-wave theory. A measuring module 830 is used to compare the detected multi-order diffraction signals with multi-order diffraction feature patterns stored in a database so as to analyze the three-dimensional structure features of an object, such as line width, height and sidewall angle. In the embodiment, the calibration module 810, the database producing module 820 and/or the measuring module 830 may be, but not limited to, an application program executed in the processing device 13.

The calibration module 810 calibrates the wavelengths of the detection light beam in the diffraction measurement system, by obtaining known structural feature values of a calibration grating that include pitches. The multi-order diffraction feature pattern information with multi-wavelengths measured by the diffraction measurement system with the calibration grating as an object is the calibration grating 811 shown in FIG. 8. The calibration module 810 can obtain each corresponding value of the multi-wavelengths $\lambda m$ of the detection light beam produced from the light source generator 10 according to the calibration multi-order diffraction feature patterns of the calibration grating 811 and the known specifications of the scattering measurement system. The known specifications of the scattering measurement system may include an incident angle qi of the detection light beam, a distance D from the location of the object 2 (i.e., the calibration grating) to the detector 12 of the scattering measurement system, and specifications of the detector 12 (e.g., sensor size, pixel size, number of pixels.)

The database producing module 820 produces multi-order diffraction feature patterns as a compared object in a database, by producing multi-order diffraction feature patterns with different wavelengths $\lambda m$ corresponding to the grating, with rigorous coupled-wave analysis (RCWA), based on wavelengths $\lambda m$ of the detection light beams, the estimated structural feature information of gratings, such as critical dimension, sidewall angle, pitch, height or line width, and process parameters of the gratings (e.g., refractive index and absorption coefficient of the grating material corresponding to different wavelengths).

The measuring module 830 measures structural feature information of any object, by obtaining multi-order diffraction signals 831 of the three-dimensional feature information of an object from the scattering measurement system, comparing the multi-order diffraction signals with the database, determining whether the root-mean-square of the comparison parameters is less than or equal to a predetermined condition $\delta$, and obtaining structural feature information corresponding to the compared multi-order diffraction feature patterns as the structural feature information used to analyze the object.

In an embodiment, the aforesaid comparison parameters may include ratios of intensity of the +1 order diffraction signal to intensity of the −1 order diffraction signal corresponding to each of the multi-wavelengths of the detection light beam. Please further refer to the two experimental examples shown in FIG. 9, Table 1 and Table 2, but the disclosure is not limited thereto.

First Experimental Example

TABLE 1

| Wavelength of detection light beam λm (unit: nm) | 34.4 | 31.6 | 29.3 | 27.28 | 25.5 |
|---|---|---|---|---|---|
| Intensity of the +1 order diffraction signal (unit: count) | 2033 | 10383 | 6277 | 1857 | 1037 |
| Intensity of the −1 order diffraction signal (unit: count) | 5391 | 5273 | 3176 | 5465 | 1998 |
| Ratio of intensity of the +1 order diffraction signal to intensity of the −1 order diffraction signal (Experimental data of the measured object) | 0.377 | 1.950 | 5.265 | 0.339 | 0.519 |
| Ratio of intensity of the +1 order diffraction signal to intensity of the −1 order diffraction signal (From database data) | 0.333 | 1.268 | 7.049 | 0.092 | 0.425 |

Figure 9:
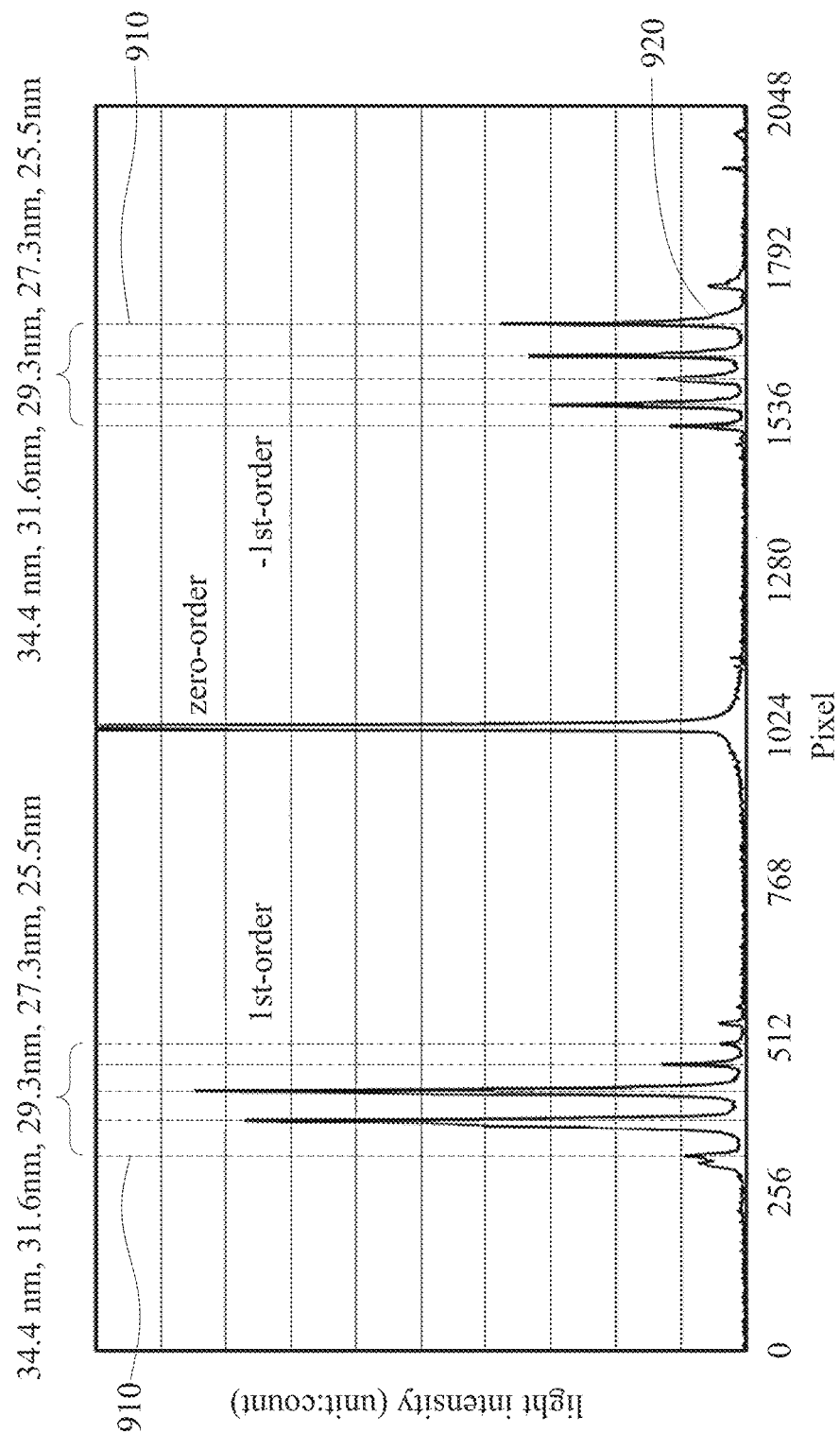
FIG. 9 is an experimental diagram of an object measured by a scattering measurement system according to an exemplary embodiment of the disclosure.

FIG. 9 is an experimental diagram showing multi-order diffraction patterns 831 of a grating object measured by the scattering measurement system according to an embodiment of the disclosure and Table 1 shows the first experimental data with respect to the first experimental example. In the first experimental example, the detection light beam generated from the light source generator 10 is HHG EUV light beam with discrete multi-wavelengths, and the discrete multi-wavelengths are respectively 34.4 nm, 31.6 nm, 29.3 nm, 27.28 nm and 25.5 nm; the incident angle of the light beam incident on the object is 45 degree; a distance D from the measured object to the detector 12 is 157 mm; the detector 12 is an CCD array sensor with 2048 pixels, the size of the CCD array sensor is 276×276 mm$^2$, and the width of each pixel is 13.5 µm (e.g., 13.5 µm/pixel).

FIG. 9 shows the feature patterns 831 of the grating by the diffraction measurement system, including a measured distribution of scattered-light intensity 920 having plural diffraction patterns therein. Wavelengths, diffraction orders and intensity of each diffraction order with respect to each wavelength can be obtained by the processing device 13 base on the information of the scattering measurement system revealed in the afore-paragraph and the aforesaid equation 1. Referring to FIG. 9, the experimental diagram shows dashed lines 910 for marking the diffraction peaks of the +1st order and −1st order diffraction signals corresponding to wavelengths 34.4 nm, 31.6 nm, 29.3 nm, 27.3 nm and 25.5 nm respectively, and intensities of the +1 order and −1 order diffraction signals are also recorded in Table 1.

In the first experimental example, a ratio of intensity of the +1 order diffraction signal to intensity of the −1 order diffraction signal is used as the afore-said comparison parameters, but not limited to, for obtaining the structure information of the grating object through comparing the database data. Referring to Table 1, the value of a root-mean-square δ1 of the comparison parameters between the experimental data and the database data is 0.52, and then the obtained structure information includes Top-CD of 381 nm, Bottom-CD of 386 nm, pitch of two adjacent grating structures of 833 nm, height of a grating structure of 202 nm.

Second Experimental Example

TABLE 2

| Wavelength of detection light beam λm (unit: nm) | 25.8 |
|---|---|
| Intensity of the +1 order diffraction signal (unit: count) | 1679 |
| Intensity of the −1 order diffraction signal (unit: count) | 24625 |
| Ratio of intensity of the +1st order diffraction signal to intensity of the −1 order diffraction signal (Experimental data of the measured object) | 0.0682 |
| Ratio of intensity of the +1st order diffraction signal to intensity of the −1 order diffraction signal (From database data) | 0.0645 |

Table 2 shows the measurement data with respect to the second experimental example. In the second experimental example, the detection light beam generated from the light source generator 10 is HHG EUV light beam with discrete multi-wavelengths, and one of the discrete multi-wavelengths is 25.8 nm; the incident angle of the light beam incident on the object is 45 degree; a distance D from the measured object to the detector 12 is 41 mm; the detector 12 is an CCD array sensor with 2048 pixels, the size of the CCD array sensor is 276×276 mm$^2$, and the width of each pixel is 13.5 µm (e.g., 13.5 µm/pixel). According to the experimental data in Table 2, the value of a root-mean-square δ2 of the comparison parameters between the experimental data and the database data is 0.525234, and then the obtained structure information includes Top-CD of 66 nm, Bottom-CD of 74 nm, pitch of two adjacent grating structures of 140 nm, height of a grating structure of 49 nm.

According to the aforementioned embodiments of the scattering measurement system and method of the present disclosure, a light beam with multi-wavelengths is incident on an object and scattered by the object to generate a plurality of multi-order diffraction light beams. The plurality of multi-order diffraction light beams with or without 0th-order diffraction light beams are converted into multi-order diffraction signals with three-dimensional feature information of the object. Further, the three-dimensional structure of the object can be accurately obtained by comparing the multi-order diffraction signals with a database. As such, the present disclosure can be used in measuring dimensions such as the line width, the height and the sidewall angle of an object.

As such, aforementioned embodiments of the present disclosure may increase the accuracy in measuring nanoscale three-dimensional structures. Therefore, embodiments of the present disclosure can be used in measuring dimensions such as the height, the sidewall angle and the gate length of a FinFET structure, and facilitate the rapid development of EUV (extreme ultraviolet) lithography processing technologies.

The above-described descriptions of the detailed embodiments are only to illustrate the preferred implementation according to the present disclosure, and it is not intended to limit the scope of the present disclosure. Accordingly, all modifications and variations completed by those with ordinary skill in the art should fall within the scope of the present disclosure defined by the appended claims.

What is claimed is:

1. A scattering measurement system, comprising:
a light source generator configured to generate a detection light beam with discontinuous multi-wavelengths, and generate, when the detection light beam is incident on an object, a multi-order diffraction light beam with three-dimensional feature information, wherein the detection light beam is a High-order Harmonic Generation (HHG) extreme ultraviolet light beam with discontinuous multi-wavelengths;
a filter configured to filter out 0th-order signals from the multi-order diffraction light beam, with the other order light remained;
a detector having a photosensitive array, and configured to receive the multi-order diffraction light beam at a time and convert the multi-order diffraction light beam into multi-order diffraction signals with the three-dimensional feature information; and
a processor configured to receive the multi-order diffraction signals, and compare the multi-order diffraction signals with multi-order diffraction feature patterns in a database and analyze the three-dimensional feature information of the object, wherein the multi-order diffraction feature patterns in the database are multi-order diffraction feature patterns with at least one of multi-wavelengths established based on a rigorous coupled-wave theory,
wherein a size and a profile of the object are measured according to a plurality of the multi-order diffraction light beams without zero-order light beams.

2. A method for measuring three-dimensional feature information of an object, comprising:
providing a detection light beam with discontinuous multi-wavelengths to the object to generate a multi-order diffraction light beam when the detection light beam passes the object, wherein 0th-order signals from the multi-order diffraction light beam are filtered out, with the other order light remained, the detection light beam is a High-order Harmonic Generation (HHG) extreme ultraviolet light beam with discontinuous multi-wavelengths;
receiving and converting, by a photosensitive array, the multi-order diffraction light beam into multi-order diffraction signals with the three-dimensional feature information; and
comparing the multi-order diffraction signals with multi-order diffraction feature patterns in a database to analyze the three-dimension feature information of the object, wherein the multi-order diffraction feature patterns in the database are multi-order diffraction feature patterns with at least one of multi-wavelengths established based on a rigorous coupled-wave theory,
wherein a size and a profile of the object are measured according to a plurality of the multi-order diffraction light beams without zero-order light beams.

* * * * *